(12) United States Patent
Gaffney et al.

(10) Patent No.: US 8,105,971 B2
(45) Date of Patent: Jan. 31, 2012

(54) PROCESS FOR MAKING CATALYSTS USEFUL FOR THE CONVERSION OF PARAFFINS TO OLEFINS

(75) Inventors: Anne Mae Gaffney, West Chester, PA (US); Ruma Ghosh, Livingston, NJ (US); Ruozhi Song, Wilmington, DE (US); Chuen Yuan Yeh, Edison, NJ (US); Tadeusz Langner, Maplewood, NJ (US)

(73) Assignee: Lummus Technology Inc., Bloomfield, NJ (US)

( * ) Notice: Subject to any disclaimer, the term of this patent is extended or adjusted under 35 U.S.C. 154(b) by 8 days.

(21) Appl. No.: 12/417,488

(22) Filed: Apr. 2, 2009

(65) Prior Publication Data
US 2010/0255985 A1    Oct. 7, 2010

(51) Int. Cl.
*B01J 23/22*    (2006.01)
*C07C 5/333*    (2006.01)

(52) U.S. Cl. ........ 502/178; 502/179; 502/205; 502/206; 502/241; 502/242; 502/243; 502/244; 502/245; 502/247; 502/303; 502/304; 502/308; 502/309; 502/310; 502/312; 585/663

(58) Field of Classification Search .................. 585/252, 585/330, 654, 663; 502/215, 311, 312, 178, 502/179, 205, 206, 241, 242, 243, 244, 245, 502/247, 303, 304, 308, 309, 310
See application file for complete search history.

(56) References Cited

U.S. PATENT DOCUMENTS

| 3,647,916 A | 3/1972 | Caesar et al. ............ 260/683.43 |
| 4,250,346 A | 2/1981 | Young et al. |
| 4,299,800 A | 11/1981 | Nishikawa et al. |
| 4,524,236 A | 6/1985 | McCain |
| 4,596,787 A * | 6/1986 | Manyik et al. ................ 502/312 |
| 4,940,826 A | 7/1990 | Font Freide et al. |
| 5,157,204 A | 10/1992 | Brown et al. |
| 5,281,745 A * | 1/1994 | Ushikubo et al. ............. 558/319 |
| 5,380,933 A * | 1/1995 | Ushikubo et al. ............. 562/549 |

(Continued)

FOREIGN PATENT DOCUMENTS

JP    07-053414    2/1995

OTHER PUBLICATIONS

English Patent Abstract of JP07-053414 from esp@cenet, Ushikubo et al., published Feb. 28, 1995, 1 page.

(Continued)

*Primary Examiner* — Wayne Langel
*Assistant Examiner* — Syed Iqbal
(74) *Attorney, Agent, or Firm* — Alix, Yale & Ristas, LLP

(57) ABSTRACT

A process for forming a catalyst useful for the production of an olefin from a hydrocarbon is disclosed. The process may include: admixing at least one of elemental metals and compounds to form a multi-metal composition comprising Mo, V, Nb, Te and at least one of Ni and Sb; adjusting the pH of the multi-metal composition by adding nitric acid; drying the acidified multi-metal composition; calcining the dried multi-metal composition; and grinding the calcined multi-metal composition. The ground multi-metal composition may then be sized or shaped to form a mixed metal oxide catalyst. Alternatively, the ground multi-metal composition may be treated with an acid, optionally annealed, and sized or shaped to form a mixed metal oxide catalyst.

20 Claims, 7 Drawing Sheets

U.S. PATENT DOCUMENTS

| | | | |
|---|---|---|---|
| 5,446,232 A | 8/1995 | Chen et al. | |
| 6,143,686 A | 11/2000 | Vizzini et al. | 502/152 |
| 6,355,854 B1 * | 3/2002 | Liu | 585/658 |
| 6,433,234 B1 | 8/2002 | Griffiths et al. | |
| 6,566,573 B1 | 5/2003 | Bharadwaj et al. | |
| 6,638,891 B2 * | 10/2003 | Karim et al. | 502/302 |
| 6,747,066 B2 | 6/2004 | Wang et al. | |
| 6,781,008 B2 * | 8/2004 | Bogan, Jr. | 558/323 |
| 6,858,768 B2 | 2/2005 | Budin et al. | |
| RE39,074 E * | 4/2006 | Borchert et al. | 562/548 |
| 7,135,603 B2 | 11/2006 | Messenger | |
| 7,319,179 B2 | 1/2008 | Lopez Nieto et al. | |
| 2002/0183198 A1 * | 12/2002 | Gaffney et al. | 502/215 |
| 2004/0063990 A1 * | 4/2004 | Gaffney et al. | 558/322 |
| 2004/0181085 A1 * | 9/2004 | Bogan et al. | 558/323 |
| 2005/0085678 A1 | 4/2005 | Lopez Nieto et al. | |
| 2007/0232828 A1 | 10/2007 | Hazin et al. | 562/400 |
| 2009/0018362 A1 | 1/2009 | Dubois | 562/542 |

OTHER PUBLICATIONS

Selective Oxidative Dehydrogenation of ethane on MoVTeNbO Mixed Metal Oxide Catalysts: by P. Botella, E. Garcia-Gonzalez, A. Dejoz, J.M. Lopez Nieto, M.I. Vazquez, and J. Gonzales-Calbet, Journal of Catalysis 225, pp. 428-438, 2004.

Preparation of MoVTe(Sb)Nb Mixed Oxide Catalysts Using a Slurry Method for Selective Oxidative Dehydrogenation of Ethane: by Q.Xie, L. Chen, W. Weng, and H. Wan, Journal of Molecular Catalysis A. 240: pp. 191-196, 2005.

Kinetics of oxidative dehydrogenation of C2-C3 alkanes on oxide catalysts: by Grabowski, R., Catal. Rev. Sci and Engg. 48, pp. 199-268, 2006.

International Search Report for International Application No. PCT/US 10/29776 filed on Apr. 2, 2010, in the name of Lummus Technology Inc.

* cited by examiner

PROCESS FOR MAKING CATALYSTS USEFUL FOR THE CONVERSION OF PARAFFINS TO OLEFINS

BACKGROUND OF DISCLOSURE

1. Field of the Disclosure

Embodiments disclosed herein relate generally to a process for forming catalysts useful for the conversion of paraffins to olefins. More specifically, embodiments disclosed herein relate to manufacture of catalysts useful for the oxidative dehydrogenation of hydrocarbons to form olefins. In yet another aspect, embodiments disclosed herein relate to a process for manufacturing mixed metal oxide catalysts useful for the oxidative dehydrogenation of ethane to form ethylene.

2. Background

Ethylene is an important petrochemical used as a raw material for the manufacture of polymers, ethylbenzene, styrene, and polystyrene, among other chemical products. Over 90% of currently produced ethylene is derived from steam cracking of naphtha and/or ethane. Ethylene may be obtained from the non-catalytic thermal cracking of saturated hydrocarbons, such as ethane and propane, and alternatively from thermal or steam cracking of heavier liquids such as naphtha and gas oil. Steam cracking produces a variety of other products, including diolefins and acetylene. The latter are costly to separate from the ethylene, usually by extractive distillation and/or selective hydrogenation of the acetylene back to ethylene. An ethylene plant using cracking typically achieves an ethylene selectivity of about 85 percent calculated on a carbon atom basis at an ethane conversion of about 60 percent. In addition, thermal cracking processes for olefin production are highly endothermic. Accordingly, these processes require the construction and maintenance of large, capital intensive and complex cracking furnaces to supply the heat.

Existing steam cracking processes generates ethylene by raising the feed (ethane or other hydrocarbons) to high enough temperature (700-1000° C.) in furnace tubes to thermally crack the hydrocarbons into olefins, especially ethylene and secondarily propylene, plus a range of other hydrocarbons, hydrogen and coke. The residence time must be very short, on the order of milliseconds, and the effluent must be quenched immediately, in order to maximize the desired olefins and minimize the undesired by-products. The pressure must be kept to a minimum, substantial steam dilution is required, and design features are critical for obtaining the best results. As a result, the reaction conditions are very sensitive, and the furnaces are very expensive, with high fuel requirement due to both the high temperature and the high endothermicity of the cracking reactions, and decoking is also a major requirement.

Autothermal cracking ("ATC") is a similar process, but with a combustion reaction added to supply the heat, as an alternative to using expensive heat transfer in furnaces. The combustion reaction includes use of a catalyst, for which the high temperature and low pressure is a severe environment. There is still very sensitive millisecond cracking reaction and quenching with a range of products, and the added combustion reaction creates additional byproducts while consuming either a portion of the feed and product and/or a combustible that is added.

An alternative is to catalytically dehydrogenate ethane in the presence of oxygen to form ethylene. The process is called oxidative dehydrogenation (ODH). In this process, the effluent contains clean ethylene with small amounts of carbon monoxide and carbon dioxide as byproducts. The oxidative dehydrogenation (ODH) of ethane is of interest for ethylene production, as ODH is thermodynamically favored and can be carried out at lower reaction temperatures without coke formation.

In U.S. Pat. No. 4,250,346, ethane is catalytically oxydehydrogenated to ethylene in a gas phase reaction, in the presence or absence of water, at temperatures of less than 550° C. The catalysts disclosed therein include oxides of molybdenum: $Mo_aX_bY_c$, where X=Cr, Mn, Nb, Ta, Ti, V and/or W, Y=Bi, Ce, Co, Cu, Fe, K, Mg, Ni, P, Pb, Sb, Si, Sn, Tl and/or U.

U.S. Pat. No. 4,524,236 discloses a catalyst useful for the production of ethylene from ethane via oxidative dehydrogenation, including oxides of molybdenum: $Mo_aV_bNb_cSb_dX_e$, where X=Li, Sc, Na, Be, Mg, Ca, Sr, Ba, Ti, Zr, Hf, Y, Ta, Cr, Fe, Co, Ni, Ce, La, Zn, Cd, Hg, Al, Tl, Pb, As, Bi, Te, U, and W. The reaction can be carried out in the presence or absence of water; however, significant amounts of acetic acid are formed in the presence of water, which results in reduced ethylene selectivity.

U.S. Pat. No. 6,858,768 discloses a catalyst useful for the production of olefins from alkanes via oxidative dehydrogenation, including an oxide selected from the group containing alumina, zirconia, titania, yttria, silica, niobia, and vanadia. As disclosed, the catalyst need higher preheat temperatures for activation.

U.S. Pat. No. 7,319,179 discloses a mixed metal oxide comprising molybdenum, vanadium, tellurium, and niobium useful as a catalyst for ODH of ethane to ethylene.

JP 07-053414 discloses use of mixed metal oxide catalyst containing transition metal elements with molybdenum, vanadium, niobium, and tellurium for the ODH of ethane to ethylene. The best selectivity reported therein is 91.5% ethylene at 56.7% conversion at a reaction temperature of 360° C.

Other patents discussing ODH of ethane to ethylene include U.S. Pat. Nos. 6,858,768, 7,135,603, 4,940,826, 6,433,234, and 6,566,573. Various other references discussing ODH include: P. Botella, E. Garcia-Gonzalez, A. Dejoz, J. M. Lopez Nieto, M. I. Vazquez, and J. Gonzalez-Calbet, "Selective oxidative dehydrogenation of ethane on MoVTeNbO mixed metal oxide catalysts," *Journal of Catalysis* 225: 428-438, 2004; Q. Xie, L. Chen, W. Weng, and H. Wan "Preparation of MoVTe(Sb)Nb mixed oxide catalysts using a slurry method for selective oxidative dehydrogenation of ethane," *Journal of Molecular Catalysis A.* 240: 191-196, 2005; and Grabowski, R. "Kinetics of oxidative dehydrogenation of C2-C3 alkanes on oxide catalysts," *Catal. Rev. Sci and Engg.* 48: 199-268, 2006.

Due to the advantages over the prior art, ODH of ethane to ethylene has been the object of considerable research. Over the years, many catalyst systems have been investigated, including carbon molecular sieves, metal phosphates, and mixed metal oxides. However, commercialization has not been possible due to low product selectivity at reasonably high ethane conversions. In many of the prior art processes using ODH to form ethylene, the oxygen has generated excessive byproducts (primarily COx), with selectivity to the desired ethylene product reaching no higher than about 85 mole % at ethane conversion of 60-70%. At this level of selectivity and conversion, no advantage over steam cracking is realized.

Accordingly, there remains a need in the art for catalysts useful in ODH processes having high selectivity at reasonably high hydrocarbon conversions.

SUMMARY OF THE DISCLOSURE

In one aspect, embodiments disclosed herein relate to a process for forming a catalyst useful for the production of an olefin from a hydrocarbon is disclosed. The process may include: admixing at least one of elemental metals and compounds to form a multi-metal composition comprising Mo, V, Nb, Te and at least one of Ni and Sb; adjusting the pH of the multi-metal composition by adding nitric acid; drying the acidified multi-metal composition; calcining the dried multi-metal composition; and grinding the calcined multi-metal composition. The ground multi-metal composition may then be sized or shaped to form a mixed metal oxide catalyst. Alternatively, the ground multi-metal composition may be treated with an acid, optionally annealed, and sized or shaped to form a mixed metal oxide catalyst.

In another aspect, embodiments disclosed herein relate to a catalyst for oxydehydrogenating a paraffin to form an olefin, where the catalyst may be formed by a process including: admixing at least one of elemental metals and compounds to form a multi-metal composition comprising Mo, V, Nb, Te and at least one of Ni and Sb; adjusting the pH of the multi-metal composition by adding nitric acid; drying the acidified multi-metal composition; calcining the dried multi-metal composition; and grinding the calcined multi-metal composition.

In another aspect, embodiments disclosed herein relate to a catalyst for oxydehydrogenating a paraffin to form an olefin. The catalyst may be of the formula: $Mo_aV_bX_cY_dZ_eO_x$, wherein: X=at least one of Nb and Ta; Y=at least one of Sb and Ni; Z=at least one of the Te, Ga, Pd, W, Bi and Al; a=1.0; b=0.05 to 1.0; c=0.001 to 1.0; d=0.001 to 1.0; e=0.001 to 0.5; n is determined by the oxidation states of the other elements. The resulting catalyst may have a selectivity to olefin of at least 85 mole % at a paraffin conversion of at least 60%.

Other aspects and advantages will be apparent from the following description and the appended claims.

DETAILED DESCRIPTION

Figure 1:
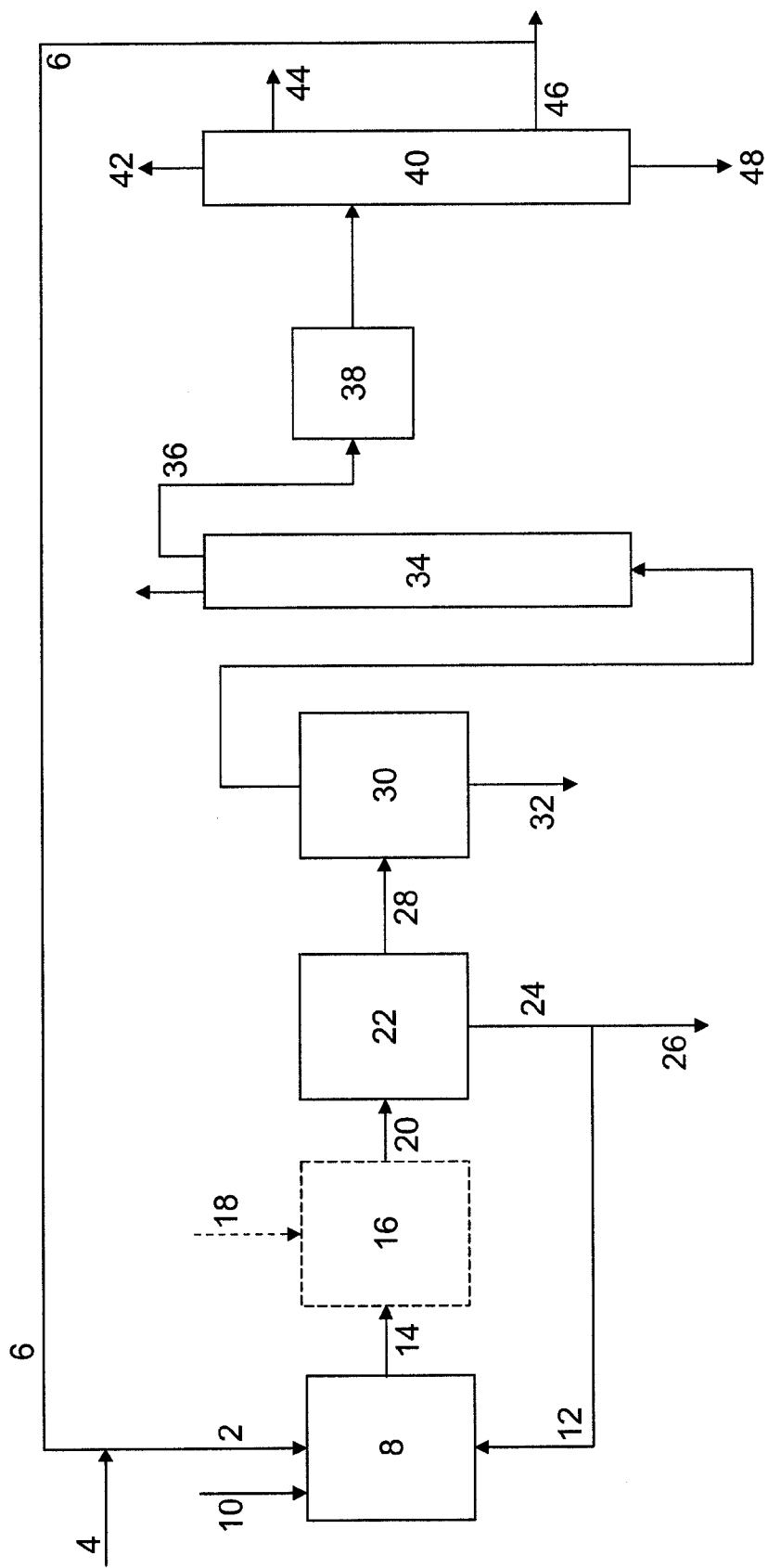
FIG. 1 is a simplified process flow diagram for oxidative dehydrogenation processes according to embodiments disclosed herein.

In one aspect, embodiments herein relate to a method to produce catalysts useful for the oxidative dehydrogenation of hydrocarbons to form olefins. More specifically, embodiments disclosed herein relate to a process for forming mixed metal oxide catalysts useful in the oxidative dehydrogenation of ethane to form ethylene. The catalysts manufacturing methods disclosed herein may result in mixed metal oxide catalysts having improved selectivity to the olefin as compared to prior art ODH catalysts. In some embodiments, catalysts prepared according to methods disclosed herein may be used in an ODH process to produce olefins with essentially no hydrocarbon byproducts and minimal production of carbon oxides.

Oxidative dehydrogenation (ODH) processes disclosed herein may be performed by contacting a hydrocarbon and an oxygen containing gas in the presence of a mixed metal oxide catalyst, prepared according to embodiments disclosed herein, under conditions to oxidize at least a portion of the hydrocarbon to produce an olefin product. The mixed metal oxide catalysts disclosed herein may be prepared in a manner such that the resulting catalyst has a high selectivity toward olefin production, even at high hydrocarbon conversions. The catalysts described herein, together with the reactor conditions reflected herein, result in high enough ethylene selectivity and conversion to provide an economical process for ODH of ethane to ethylene.

Catalysts disclosed herein useful for ODH of a paraffin to form an olefin may have an olefin selectivity of at least 85 mole % at a paraffin conversion of at least 60%. In some embodiments, catalysts disclosed herein may have an olefin selectivity of at least 88 mole % at a paraffin conversion of at least 60%; an olefin selectivity of at least 90 mole % at a paraffin conversion of at least 60% in other embodiments; in other embodiments, catalysts disclosed herein may have an olefin selectivity of at least 90 mole % at a paraffin conversion of at least 65%; an olefin selectivity of at least 90 mole % at a paraffin conversion of at least 70% in other embodiments; and an olefin selectivity of at least 90 mole % at a paraffin conversion of at least 75% in yet other embodiments.

For example, when used for the oxidative dehydrogenation of ethane to ethylene, catalysts disclosed herein may have an ethylene selectivity of at least 85 mole % at an ethane conversion of at least 60%. In some embodiments, catalysts disclosed herein may have an ethylene selectivity of at least 88 mole % at an ethane conversion of at least 60%; an ethylene selectivity of at least 90 mole % at an ethane conversion of at least 60% in other embodiments; in other embodiments, catalysts disclosed herein may have an ethylene selectivity of at least 90 mole % at an ethane conversion of at least 65%; an ethylene selectivity of at least 90 mole % at an ethane conversion of at least 70% in other embodiments; and an ethylene selectivity of at least 90 mole % at an ethane conversion of at least 75% in yet other embodiments. The catalysts and the ODH processes of embodiments disclosed herein are described in more detail below.

In some embodiments, catalysts disclosed herein may have an ethylene selectivity of at least 85, 90, 91, 92, 93, 94, 95, 96, or 97 mole % at an ethane conversion of at least 40, 45, 50, 55, or 60%, where any ethylene selectivity limit may correspond to any ethane conversion limit. The high selectivity toward ethylene in embodiments disclosed herein may result in improved process economics over prior art processes, even at lower ethane conversions.

Catalyst

Catalysts prepared according to embodiments disclosed herein, useful for ODH of paraffins to form olefins, may include a mixed metal oxide catalyst having a general formula:

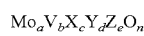

wherein: X=at least one of Nb and Ta; Y=at least one of Sb and Ni; Z=at least one of the Te, Ga, Pd, W, Bi and Al; a=1.0; b=0.05 to 1.0; c=0.001 to 1.0; d=0.001 to 1.0; e=0.001 to 0.5; and n is determined by the oxidation states of the other elements.

In other embodiments, catalysts prepared according to embodiments disclosed herein, useful for ODH of paraffins to form olefins, may include a mixed metal oxide catalyst having a general formula:

$$Mo_a V_b X_c Y_d Z_e M_f O_n$$

wherein: X=at least one of Nb and Ta; Y=at least one of Sb and Ni; Z=at least of one of the Te, Ga, Pd, W, Bi and Al; M=at least one of Fe, Co, Fe, Cu, Cr, Ti, Ce, Zr, Mn, Pb, Mg, Sn, Pt, Si, La, K, Ag and In; a=1.0; b=0.05 to 1.0; c=0.001 to 1.0; d=0.001 to 1.0; e=0.001 to 0.5; and f=0.001 to 0.3; and n is determined by the oxidation states of the other elements.

It has surprisingly been found by the present inventors that the above catalysts may provide for improvements in selectivity and conversion of paraffins to olefins in oxidative dehydrogenation processes when prepared in accordance with preparation methods disclosed herein.

Other catalysts compositions, such as those disclosed in JP 07-053414, U.S. Pat. No. 4,524,236, and U.S. Pat. No. 7,319,179, may also be used, so long as the catalyst compositions are prepared in accordance with procedures disclosed herein. Each of these is incorporated herein to the extent not contradictory with catalyst preparation methods disclosed herein.

The above described catalysts may be prepared by a process including at least the following steps. In a first step, compounds of the different metals, or pure elements, or of a mixture of both may be admixed. The admixing may be performed starting from the compounds of the different elements, starting from the actual pure elements in solution, or by hydrothermal methods.

The elements Mo, V, Nb, Sb, and Te can be incorporated into the admixing step as pure metallic elements, as salts, as oxides, as hydroxides, as alkoxides, as acids, or as mixtures of two or more of the above-mentioned forms. As salts, sulphates, nitrates, oxalates, halides, or oxyhalides may be used. For example, the Mo can be incorporated at the mixing stage as molybdic acid, ammonium heptamolybdate, molybdenum chlorides, molybdenum acetate, molybdenum ethoxide and/or molybdenum oxides. The V can be incorporated at the admixing step, for example, as ammonium vanadate, vanadium oxide, vanadyl sulphate, vanadyl oxalate, vanadium chloride or vanadyl trichloride. The Nb can be incorporated at the admixing step, for example, as niobium pentoxide, niobium oxalate, niobium chloride or Nb metal. The Sb can be incorporated at the admixing step, for example, as antimony oxalate, antimony oxide, antimony chloride and antimony acetate. The Te can be incorporated at the admixing step, for example, as telluric acid, tellurium dioxide, tellurium ethoxide, tellurium chloride and metallic tellurium.

The elements Ta, Ni, Pd, W, Ga, Al, Cu, Bi, Sn, Fe, Co, rare earth, alkaline metals or alkaline earth metals may also be incorporated at the admixing step as salts, oxides, hydroxides or alkoxides, pure or as mixtures of two or more elements. In some embodiments, they may be incorporated as sulphates, nitrates, oxalates or halides.

The above elements and compounds may be combined to form one or more solutions or slurries, which may be subsequently admixed.

Nitric acid is used to adjust the pH of the resulting admixture or an initial admixture to be combined with additional solutions or slurries to form the desired catalyst composition. For example, in some embodiments, a solution including all desired compounds may be formed and the pH adjusted using nitric acid. As another example, in some embodiments, a first solution may be formed including a subset of the desired compounds, and a second solution may be formed including a subset of the remaining compounds; the first or second solution may then be mixed with nitric acid and the first and second solutions then admixed to result in the desired catalyst composition.

The admixing step may be followed by a period of static permanence in the reactor, or the mixing may be carried out with stirring. Both the static permanence and the stirring may be done in a normal reactor or in an autoclave. The admixing step may be carried out in solution, such as in deionized water, or by means of hydrothermal treatment.

The resulting admixture may then be dried. Drying may be carried out by conventional methods in a kiln, evaporation with stirring, and evaporation in a rotavapor, vacuum drying, freeze drying, or spray drying, among other methods. In some embodiments, the first and second solutions or slurries and/or the nitric acid may be fed to the drying apparatus separately.

The dried solids may then be calcined. Calcination of the dry solid can be carried out in an inert gas atmosphere, such as for example nitrogen, helium, argon or mixtures, of air or mixtures.

An alternative embodiment of the method is, as stated earlier, carried out by employing hydrothermal methods (containing two or more elements in the synthesis, especially containing Mo, V, Te, Sb, and Nb). The synthesis temperature and time may be determining conditions used during hydrothermal methods. The synthesis temperature may be within the range from about 100° C. to about 250° C. in some embodiments, and from about 150° C. to about 200° C. in other embodiments. The synthesis time may be within the range from about 6 to about 500 hours in some embodiments, and from about 24 to about 200 hours in other embodiments. Hydrothermal treatments may also be staged; for example, Te and Mo compounds may be mixed and treated first, followed by addition of other compounds and a second hydrothermal treatment.

Calcination may be carried out by causing a flow of inert gas to pass (with spatial velocities between 1 and 400 h$^{-1}$) or statically. Calcination temperatures may range from about 250° C. to about 1000° C. in some embodiments, and from about 400° C. to about 800° C. in other embodiments. The calcination time is not a determining factor, though calcination times may range from about 0.5 hours to about 20 hours. The speed of heating is not a determining factor, though between 0.1° C./minute to about 10° C./minute is typical. The catalyst may also be initially calcined in an oxidizing atmosphere at a temperature up to about 350° C. in some embodiments, and within the range from about 250° C. to about 300° C. in other embodiments, and later be subjected to calcination in an inert atmosphere.

Various elements, such as Ta, Ni, Pd, W, Ga, Al, Cu, Bi, Sn, Fe, Co, rare earth, alkaline metals or alkaline earth metals may also be incorporated after the calcination stage by impregnation or precipitation. In this case, the resulting solid will be subjected to a second calcination stage.

The resulting solids formed by the above described methods exhibit good catalytic activity and selectivity by itself. However, the solid may be converted to a catalyst having higher activity and selectivity by grinding. There is no particular restriction as to the grinding method. It can be conventional methods, for example, dry milling, wet milling, cryogenic milling and jet milling. The grinding may be conducted not only mechanically, but using a mortar or the like in the case of a small scale operation. It is preferred that the ground powder has a BET surface area in the range of 5-30 m$^2$/g; more preferably the BET surface area is in the range of 8-20 m$^2$/g.

The ground solid may be used as final catalyst after shaping and sizing. It is also possible to further tailor the catalytic activity and selectivity by acid treatment, either prior to or following shaping and sizing of the catalyst. Such treatment may be effected without any particular restrictions. Suitable acids for the treatment may be organic acids and inorganic acids. As organic acids, oxalic acid, formic acid, malonic acid, acetic acid, citric acid, and tartaric acid may be used, however, oxalic acid is preferred. As inorganic acids, sulfuric acid, nitric acid, hydrochloric acid and phosphoric acid may be used. If the acid is a liquid, it may be used as is or dissolved in a solvent. If the acid is a solid, it is used as a solution in a solvent. Suitable solvent may be water, methanol and ethanol. When using solutions, there is no particular restriction on the concentration of the acid. Normally, the concentration of the acid in the solution can vary from 0.1 to 50% by weight, preferably 1-10% by weight. The acid solution is normally used in an amount of 1 to 100 times the volume of the ground catalyst powder, preferably 3 to 50 times the volume, more preferably 5 to 25 times the volume. Normally, treatment temperatures of room temperature to 200° C. are utilized, preferably 50° C. to 150° C., more preferably 60° C. to 100° C. The treatment time will be affected by the temperature at which the treatment is carried out. Normally, the treatment times of 1 to 100 hours are utilized, preferably 2 to 20 hours. In some embodiments, an acid treatment step may be combined with a grinding step via a wet milling process.

The solid obtained by the above-mentioned method may be used as a final catalyst, but it may further subjected to heat treatment usually at a temperature in the range of 300° C. to about 500° C., such as about 400° C., for a time period of at least 1 hour.

The solid thus obtained may be used by itself as a solid catalyst, but may be formed into a catalyst together with a suitable support such as silica, alumina, silica-aluminas, aluminosilicates, zirconia, titania, boria, zirconia toughened alumina, lithium aluminum silicates, silicon carbide, oxide-bonded silicon carbide, and mixtures thereof. Further, it may be molded into a suitable shape and particle size depending on the scale or system of the reactor.

The resulting solid formed by the above described methods may then be sized and formed into a desired catalyst particle. Sizing may include grinding of the solids to form a powder. The resulting powder may then be pressed and sized to form, for example, granules. In some embodiments, the granules are formed to be within the 12-20 mesh size range.

In other embodiments, the above catalysts may be formed on a support. Suitable supports for the catalyst include silica, alumina, silica-aluminas, aluminosilicates, zirconia, titania, boria, zirconia toughened alumina, lithium aluminum silicates, silicon carbide, oxide-bonded silicon carbide, and mixtures thereof. When used on a support, the supported catalyst usually comprises from about 5 to 50% by weight of the catalyst composition, with the remainder being the support. When the catalyst is to be used with a support, in some embodiments it is desirable to filter the combined solution to remove the insoluble portion before impregnating the support.

In other embodiments, catalysts formed according to the processes described above may undergo one or more acid treatment and/or annealing stages. For example, calcined catalysts or sized catalysts particles may be contacted with a carboxylic acid, such as oxalic acid. The resulting solids may then be dried and sized, if necessary. If necessary, annealing, for example, may be performed by heating the acid-treated catalyst to a temperature in the range of 300° C. to about 500° C., such as about 400° C., for a time period of at least 1 hour.

Oxidative Dehydrogenation

The processes disclosed herein may be used to convert both liquid and gaseous hydrocarbons into olefins. Suitable liquid hydrocarbons include naphtha, gas oils, vacuum gas oils, refinery residues, atmospheric residues, vacuum residues, crude oils, fuel oils, natural gas, and mixtures thereof. In some embodiments, gaseous hydrocarbons such as ethane, propane, butane and mixtures thereof are used. Suitably, the hydrocarbon is a paraffin-containing feed including hydrocarbons having at least two carbon atoms. In some embodiments, processes disclosed herein may be used to convert ethane to ethylene.

Hydrocarbon feeds including ethane may be from any number of sources, including natural gas, provided that impurities are removed sufficiently to prevent catalyst poisons and eventual product contaminants, and also to avoid economically excessive content of accompanying hydrocarbons. This can be accomplished by conventional means known to those skilled in the art.

Other ethane feed sources may include ethane byproduct from a pyrolysis plant (steam cracker, autothermal cracker) that might otherwise be recycled to the pyrolysis plant for further cracking to ethylene. Instead, this pyrolysis ethane can be fed to ethane ODH processes disclosed herein. Typically, this pyrolysis ethane is already at a very high purity and is excellent feed to ethane ODH processes disclosed herein.

The feed to the ethane ODH reactor may include fresh ethane, such as from sources mentioned above, and may also include recycle of unreacted ethane recovered from the ODH reactor effluent.

The oxygen-containing gas may include air, oxygen, and/or an air/oxygen mixture. Oxygen may be "pure oxygen" or semi-pure oxygen from an oxygen plant, e.g., air separation plant, or any other suitable source. The ratio of molecular oxygen to hydrocarbon (e.g., ethane) in the feed for ODH processes disclosed herein may be within the range from about 0.01:1 to about 1:1.

The oxygen-containing gas may be mixed with an inert gas such as nitrogen, helium or argon. Additional feed components such as hydrogen, carbon monoxide, carbon dioxide and steam may also be included. The content of inert components (nitrogen, etc.) in the oxygen-containing gas need not be below any specific limit. However, it is economically advantageous that the inert content be limited, such as to below 10 mole % relative to the oxygen in some embodiments; below 5 mole % relative to the oxygen in other embodiments; and below 2 mole % relative to oxygen in yet other embodiments. Limiting inert components may reduce costs associated with effluent separation systems that may be required.

Steam may be provided in sufficient quantity to act as a heat diluent, limiting reaction temperature rise, hot spots, and to avoid formation of a flammable feed mixture. A typical feed composition, for example, may be 15 mole % ethane, 8 mole % oxygen, and 77 mole % water (steam), neglecting contents of minor constituents. Such a feed composition is suitable for operation with a conversion of about 70%; thus, the 15 mole % feed ethane may include about 10.5 mole % fresh ethane and 4.5 mole % recycle ethane.

The concentration of oxygen in the feed is limited with a margin below the minimum oxygen for combustion (by using sufficient steam) in order to have a non-flammable feed mixture, and the feed ratio of ethane to oxygen is set appropriately to obtain the desired combination of conversions of ethane and oxygen. Use of a large content of steam as diluent provides considerable advantages for its heat dilution capacity and also for reducing the flammability envelope (increasing the minimum oxygen for combustion), but increases processing costs.

The feed components, ethane, oxygen, water, etc., may be vaporized, preheated and mixed to the extent practical prior to feeding to the ODH reactor. This can be accomplished by means known to those skilled in the art. Preheat techniques may include, for example, heat exchange from steam, a heat transfer fluid, reactor effluent, and a furnace.

The ODH reactor may be a fixed-bed reactor with high heat removal, such as a multi-tube shell-and-tube reactor/heat exchanger with catalyst and process flow inside the tubes and a heat transfer fluid (or steam generation) circulated in the shell side. Another example is a plate-and-frame reactor/heat exchanger, such as a "Thermoplate Reactor" with catalyst and process flow in the channels on one side of a plate and a heat transfer fluid in the channels on the other side of the plate, having alternating plates and channels. Another example of a suitable reactor includes a micro-channel reactor/heat exchanger.

As an alternative, the ODH reactor may be a fluidized-bed reactor with high heat removal. A fluidized-bed reactor results in greater isothermicity, avoidance of hot spots, and may also have the feeds introduced separately, without pre-mixing. This can eliminate constraints on overall feed concentration related to hot spots and flammability, and allow the use of a much higher concentration of primary reactants (ethane and oxygen), with a corresponding reduction in steam for dilution. Various fluidized-bed reactor systems may be used, including dense bed (from gently bubbling up to turbulent bed), highly expanded bed ("fast fluid bed" or "circulating fluid bed"), entrained flow ("riser" or "downer"), or combinations. Heat removal can be to a heat transfer fluid or steam generation, through coils submerged in the bed and/or freeboard (above the bed), through the vessel wall, from a connected vessel with the catalyst particles transferred from one vessel to the other, etc.

One or more of the feeds may be fed in stages; i.e., a portion at the reactor inlet, a further portion at some midpoint, etc. This can be done to some extent with fixed-bed reactors, particularly if several catalyst stages are used (stage 1, stage 2, etc.). It is especially feasible in a fluidized-bed reactor system.

The reactor system may include a single stage or there may be several stages. The stages may be of the same type (fixed bed, fluidized bed) or can be of different types. The catalyst or its concentration (e.g., mixed with some solid diluent) contained in each may be the same or different. The temperature in each reaction stage may be the same or different. As noted above, a portion of one or more feed component may be delayed to a later stage. A later stage may serve as a "quench" stage, e.g., with lower temperature or with added water.

The heat that is removed from the reactor may be transferred to reactor feed heatup or to a heat transfer fluid for subsequent heat transfer. The removed heat may also be used for steam generation (or boiler feed water preheat) for use as an energy source, including steam itself or further transformed into power. Energy export to an adjacent air separation plant that provides the oxygen feed may be particularly synergistic.

The effluent from the reactor will typically contain ethylene, added water, if used, and additional water formed by the ODH reaction, COx and small amounts of other impurities (from the feed and from additional reactions) in addition to residual amounts of unreacted ethane and oxygen.

The effluent oxygen concentration from reaction stage(s) may be important for controlling the performance (i.e., selectivity and conversion) of the stage(s). The oxygen conversion is a key reaction result and may be used to determine residence times and temperatures. In addition, the oxygen partial pressure throughout each reactor stage is important for the catalyst in terms of both the catalyst reactive state (ideal oxidation level) for most active and selective performance and also long-term, stable performance by preventing coking.

In some embodiments, it may be advantageous to include an oxygen elimination reactor downstream of the ethane ODH reactor in order to allow even higher oxygen concentrations (within a moderate range) in the ethane ODH reactor effluent and thereby obtain better conditions in the ethane ODH reactor for the catalyst quantity (lower since lower oxygen conversion is required), performance, stability and life, and overall optimum ethane conversion and ethylene selectivity and yield as well. Processes useful for removal of oxygen from hydrocarbon streams may include those disclosed in U.S. Pat. Nos. 4,299,800, 5,157,204, and 6,747,066, among others, for example.

The ethane ODH reactor effluent oxygen concentration may be in the range of 0.1-2.0 mole % in some embodiments. The inclusion of an oxygen elimination reactor is especially advantageous for ethane ODH reactor effluent oxygen concentration above 0.5 mole %, but it may be used when the reactor effluent oxygen concentration is lower as well.

One type of oxygen elimination reactor uses an oxidation catalyst to have the oxygen in the ethane ODH reactor effluent combust any CO plus a portion of the ethylene and unconverted ethane. The combustion of the C2s represents yield loss, but is not excessive when the ethane ODH reactor effluent oxygen concentration is not higher than 1-2 mole %, considering that the consumption of ethane and ethylene during complete combustion to $CO_2$ and $H_2O$ is only 0.29 and 0.33 moles/mole oxygen consumed, respectively. The catalyst, conditions, and conversions cited in U.S. Pat. No. 5,446,232 are illustrative of an appropriate system. This includes a reactor temperature of 200-300° C., thus equal to or cooler than the ethane ODH reactor. Cooling the ethane ODH reactor effluent prior to the oxygen elimination reactor is highly appropriate and compatible. Of course, it is preferred for the oxygen elimination reactor to obtain complete combustion of CO and whatever amount of C2s to $CO_2$ and $H_2O$ rather than CO and $H_2$. This is to minimize consumption of the C2s for combustion and also to minimize the CO in the final effluent.

Like the ethane ODH reactor, the oxygen elimination reactor may be any of various types of reactors (fixed bed, fluid bed). It is preferable that it also have high heat removal capability, as the heat release can otherwise produce a large temperature rise, especially if the inlet oxygen concentration is higher than 0.5 mole %. On the other hand, since the inlet oxygen concentration is much lower than the overall inlet to the ethane ODH reactor, flammability is no longer an issue and the advantage of a fluidized bed is not as strong for the oxygen elimination reactor from that perspective.

The oxygen elimination reactor can be in a separate vessel from the ethane ODH reactor, or a possible embodiment is for it to be in the same vessel, e.g., as a final "stage" (especially if it is the same type reactor). An advantage of using separate vessels is the ability to handle the oxygen elimination catalyst differently from the ethane ODH catalyst, e.g., if there is a need for more frequent regenerations or replacements. Additionally, in some embodiments, there may be more than one oxygen elimination reactor in parallel, allowing catalyst in one to be regenerated or changed while the other is on-line, without shutting down the ethane ODH reactor.

An option for the oxygen elimination reactor is to add a combustible to the oxygen elimination reactor feed, e.g., $H_2$ or a hydrocarbon, in order to both [a] facilitate the combustion consumption of the oxygen and [b] consume the added combustible rather than the more valuable ethylene or residual ethane, especially to the extent that the oxygen elimination catalyst and conditions can obtain selective combustion of CO and the added combustible relative to the C2s.

Another type of oxygen elimination reactor is for it to be a final ethane ODH stage with significantly different conditions from the main ethane ODH stage(s), in these embodiments, operated to drive the oxygen to elimination, while still producing more ethylene by ODH. Such different operation may be with the same or different catalyst and may be in the same vessel or one or more separate vessel(s), as described above for the first type of oxygen elimination reactor.

Another option is to use both a final ethane ODH stage with its emphasis on driving the oxygen toward elimination followed by an oxygen elimination reactor using combustion. Again, these stages or reactors may be in separate vessels or some stages/reactors combined into a common vessel.

Yet another type of oxygen elimination reactor may incorporate addition of $H_2$ and a hydrogenation catalyst to hydrogenate the oxygen (rather than oxidation catalyst to accomplish combustion). Such a system may have additional benefit of hydrogenating various by-products to the extent that some may be present, such as acetylene and oxygenates.

The effluent from the ethane ODH reactor, and thereafter from the oxygen elimination reactor, if used, will have a high content of $H_2O$, particularly for operation at high ODH conversion if a fixed-bed reactor system is utilized (operation at low ODH conversion with high ethane recycle and feed concentration, or highly concentrated with a fluidized bed reactor system, can have much lower $H_2O$ concentrations). The effluent may be cooled and much of its water content condensed prior to compressing the gases. The condensed water may be recycled as steam content of the reactor feed. Net water generated by reaction is purged from the system.

The condensation of the large amount of effluent water greatly reduces the flow rate of the remaining vapor phase and correspondingly results in a large increase in the concentration of the non-condensing components. This may result in a decrease for the cost of the subsequent processing. However, it is important to recognize that any oxygen that might be present (especially if there is no oxygen elimination reactor prior to water condensation, or to the extent that the oxygen elimination is less than 100% complete) will become much higher than before the water condensation. This concentrating effect on the non-condensing vapor will increase further with successive processing, i.e., compression and further water knock-out, removal of $CO_2$, and eventually condensation of the hydrocarbons (including the ethane and ethylene) in the recovery system. An apparently low concentration of oxygen in the effluent from the ethane ODH reactor (subsequent to any oxygen elimination reactor) can become a high and possibly flammable concentration in downstream processing. This has important impacts for the design and operation of the recovery system, and is a reason that it is important to accomplish the oxygen elimination to a high level prior to the steps that condense and remove the condensable components.

If the oxygen elimination has been less than 100%, it may be appropriate to add an oxygen absorber for final removal prior to the condensation of hydrocarbons. An alternative approach may be to leave a small amount of oxygen in the stream and add some gaseous diluent (e.g., nitrogen or methane) at that point to avoid emergence of a gas stream which is self-flammable (inside the flammability envelope without requiring additional oxygen or combustible). If methane is used, the final off-gas may be utilized as a fuel gas. If nitrogen is used, the nitrogen may be obtained from the same air separation plant that provides the oxygen for the ethane ODH reactor.

It has been mentioned above that the oxygen elimination reactor may accomplish some additional goals related to eliminating undesirable byproducts, such as CO, acetylene, and oxygenates. Nevertheless, it may still be advantageous or necessary to incorporate appropriate processing steps downstream of the water condensation and compression for their ultimate removal by means known to those skilled in the art.

Following oxygen elimination, water separation, carbon dioxide recovery, and nitrogen separation, each where required, the ethylene product may be separated from the residual ethane, any heavy byproducts, light byproducts and residual gases, plus impurities that boil close to the product ethylene and the ethane that is recycled, by means known to those skilled in the art. As a benefit of the small amount of the compounds other than ethylene and ethane generated using processes and catalysts disclosed herein, the separations may be accomplished with less investment and operating cost than for conventional steam cracking of ethane. The byproduct $CO_2$ may be readily removed by conventional absorption techniques.

The major compounds whose separation has greatest impact on the cost are the unconverted ethane for recycle and the dilution water, also for recycle, both of which are dependent on the conversion per pass that is utilized and the corresponding appropriate feed composition. The ethane recycle rate has its largest impact for operation at low ethane conversion per pass, while the steam rate has its largest impact at high ethane conversion per pass, in conjunction with a fixed-bed ethane ODH system. The cost impact of the steam rate can be reduced at high ethane conversion per pass (thus minimal ethane recycle cost) if a fluidized-bed ethane ODH reactor system is used.

Equipment that may be used in the process described above includes conventional reactors, etc., at moderate conditions. They are amenable and economical for use in process plants that can be either large or small, unlike standard steam cracking whose complex furnace reactors are economical only when built for very large plants.

The ODH catalysts described herein enables the use of much less severe and sensitive conditions, at temperatures within the range from about 150° C. to about 500° C.; from about 300° C. to about 450° C. in other embodiments, at practical superficial residence times in the range of 0.1-10 seconds, without criticality of quick quenching, at a moderate positive pressure of about 0.1-30 bar; 0.1 to 20 bar in other embodiments. The reaction is exothermic, such that temperature control is by conventional heat removal at the temperature range mentioned, with convenient transfer to inexpensive steam cogeneration, with side benefit of its energy for heat and/or power utilization. With the moderate conditions (and the catalyst characteristics), the catalyzed ODH reaction may be accomplished with avoidance of multiple side reactions.

At the moderate reactor and effluent conditions, it is possible to control the effluent to contain a finite optimum oxygen partial pressure rather than be essentially absent. This provides a benefit for the catalyst in terms of both the catalyst reactive state (ideal oxidation level) for most active and selective performance and also long-term, stable performance by preventing coking.

The ODH effluent resulting from processes disclosed herein typically requires separate processing through some initial steps, but may also be integrated with pyrolysis plant product gas separation and purification systems in downstream steps. This approach may be economically preferred when incorporated into the original design of a pyrolysis plant with further conversion of its pyrolysis ethane to additional ethylene, due to both higher overall selectivity/production of ethylene and lower investment, than when a pyrolysis ethane recycle cracker is utilized. Processes disclosed herein may also be used to retrofit an existing pyrolysis plant and release capacity of existing recycle ethane cracking furnace(s) and their portion of the existing compression train for those to be used for increasing the feed rate of the pyrolysis plant and overall ethylene production for the retrofitted plant.

Referring now to FIGS. 1-4, various ODH processes according to embodiments disclosed herein are illustrated, where like numerals represent like parts. Referring now to FIG. 1, hydrocarbon stream 2, including fresh hydrocarbon 4 and recycle hydrocarbon 6, if used, may be fed to oxidative dehydrogenation reactor 8, which includes oxidative dehydrogenation catalysts as disclosed herein, such as in a packed, fluidized, or circulating bed. An oxygen-containing gas 10, such as air, and dilution steam 12 may also be fed to oxidative dehydrogenation reactor 8. Contact of the hydrocarbon and oxygen in the presence of the catalyst at appropriate reaction conditions, as described above, converts at least a portion of the hydrocarbon to olefins, water, and reaction byproducts, if present. The reactor effluent, which may include nitrogen, olefins, water, as well as unreacted oxygen and unreacted hydrocarbons may be recovered via flow stream 14.

If necessary or desired, the reactor effluent may then be fed via flow stream 14 to an oxygen elimination reactor 16, providing for combustion of the remaining oxygen. Additionally, added fuel, such as hydrogen or other light hydrocarbons, such as methane, may be added via flow line 18 to limit unwanted combustion of olefins and feed hydrocarbons.

Effluent from the oxygen elimination reactor may be recovered via flow line 20 and fed to quench unit 22 to reduce the temperature of the reactants so as to prevent additional formation of undesired byproducts. Water may be recovered from quench unit 22 via flow line 24, at least a portion of which may be recycled to oxidative dehydrogenation reactor 8 via flow line 12. Water not recycled may be recovered via flow line 26.

The hydrocarbons, dilution gases, such as nitrogen, if used, and byproduct gases, such as carbon oxides, may then be fed via flow line 28 to compression unit 30, where compression of the gases may result in removal of additional water recovered via flow line 32. The resulting compressed stream may then be processed to separate carbon dioxide from the hydrocarbons in $CO_2$ removal unit 34. The remaining components, including unreacted hydrocarbons, olefins, and light and heavy byproducts may then be fed via flow line 36 through dryer 38 and to separation unit 40, where light byproducts 42, olefins 44, unreacted hydrocarbons 46, and heavy byproducts 48 may be separated. At least a portion of the recovered unreacted hydrocarbons 46 may be recycled to oxidative dehydrogenation reactor 8 via recycle line 6, as mentioned above.

Figure 2:
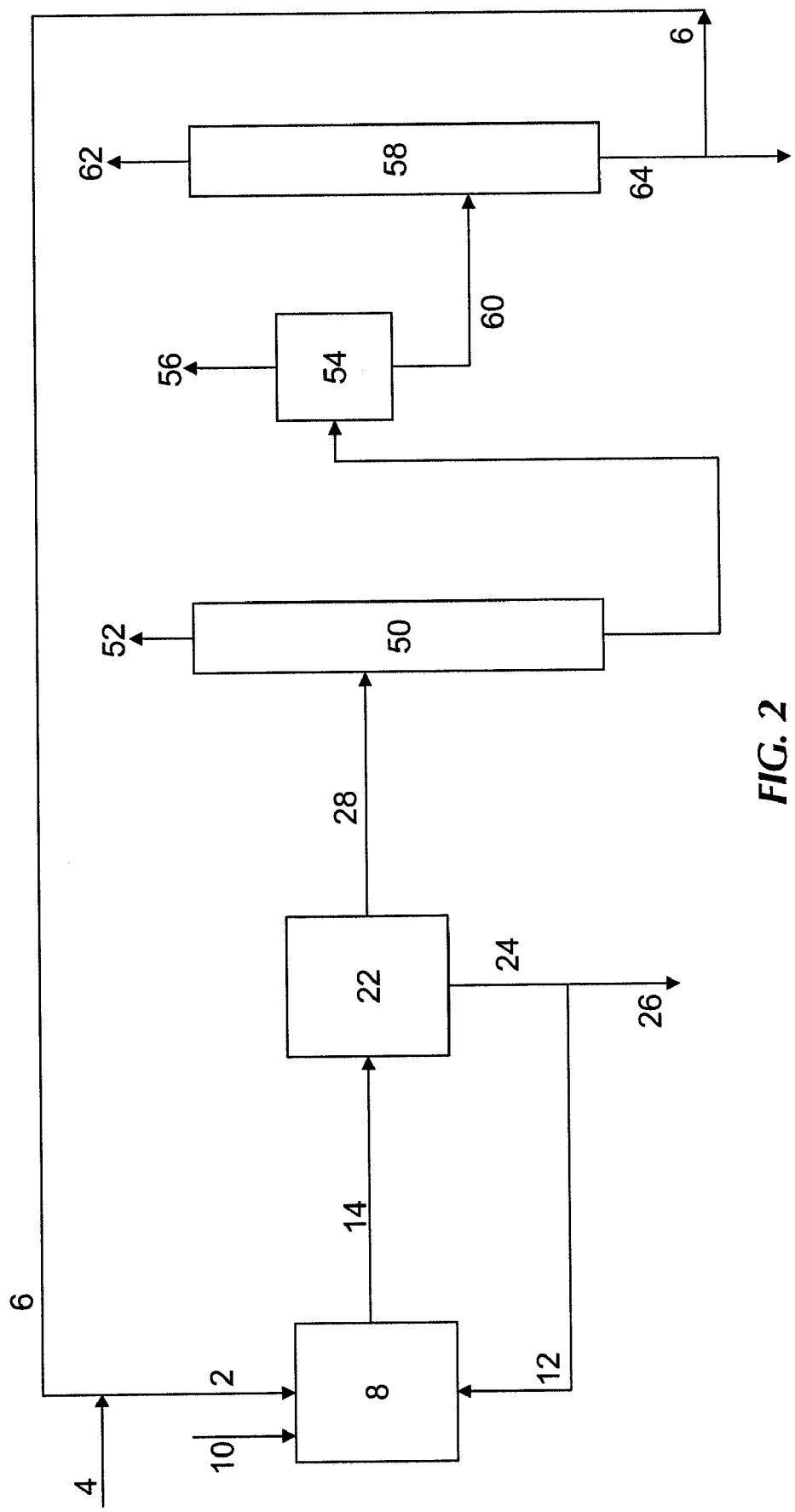
FIG. 2 is a simplified process flow diagram for oxidative dehydrogenation processes according to embodiments disclosed herein.

Referring now to FIG. 2, ethane feed stream 2, including fresh ethan 4 and recycle ethan 6, if used, may be fed to oxidative dehydration reactor 8, which includes oxidative dehydrogenation catalysts as disclosed herein, such as in a packed, fluidized, or circulating bed. An oxygen-containing gas 10, such as air, and dilution steam 12 may also be fed to oxidative dehydrogenation reactor 8. Contact of the ethane and oxygen in the presence of the catalyst at appropriate reaction conditions, as described above, converts at least a portion of the ethane to ethylene, water, and reaction byproducts, which may be present in minor quantities. The reactor effluent, which may include nitrogen, ethylene, water, as well as unreacted oxygen and unreacted ethane may be recovered via flow stream 14 and quenched via quench unit 22, as described above with respect to FIG. 1.

In this embodiment, carbon dioxide remaining in the resulting hydrocarbon stream 28, which also includes unreacted ethane and ethylene, may be separated, such as in an amine system 50. Carbon dioxide may be recovered via flow stream 52, and the hydrocarbons, including ethane and ethylene, may then be compressed and dried, and separated from nitrogen, if used, via separation unit 54. Nitrogen may be recovered via flow stream 56 and the ethane/ethylene mixture may then be forwarded to separation unit 58 via flow stream 60 to separate the ethylene 62 from unreacted ethan 64, a portion of which may be recycled via flow line 6.

Figure 3:
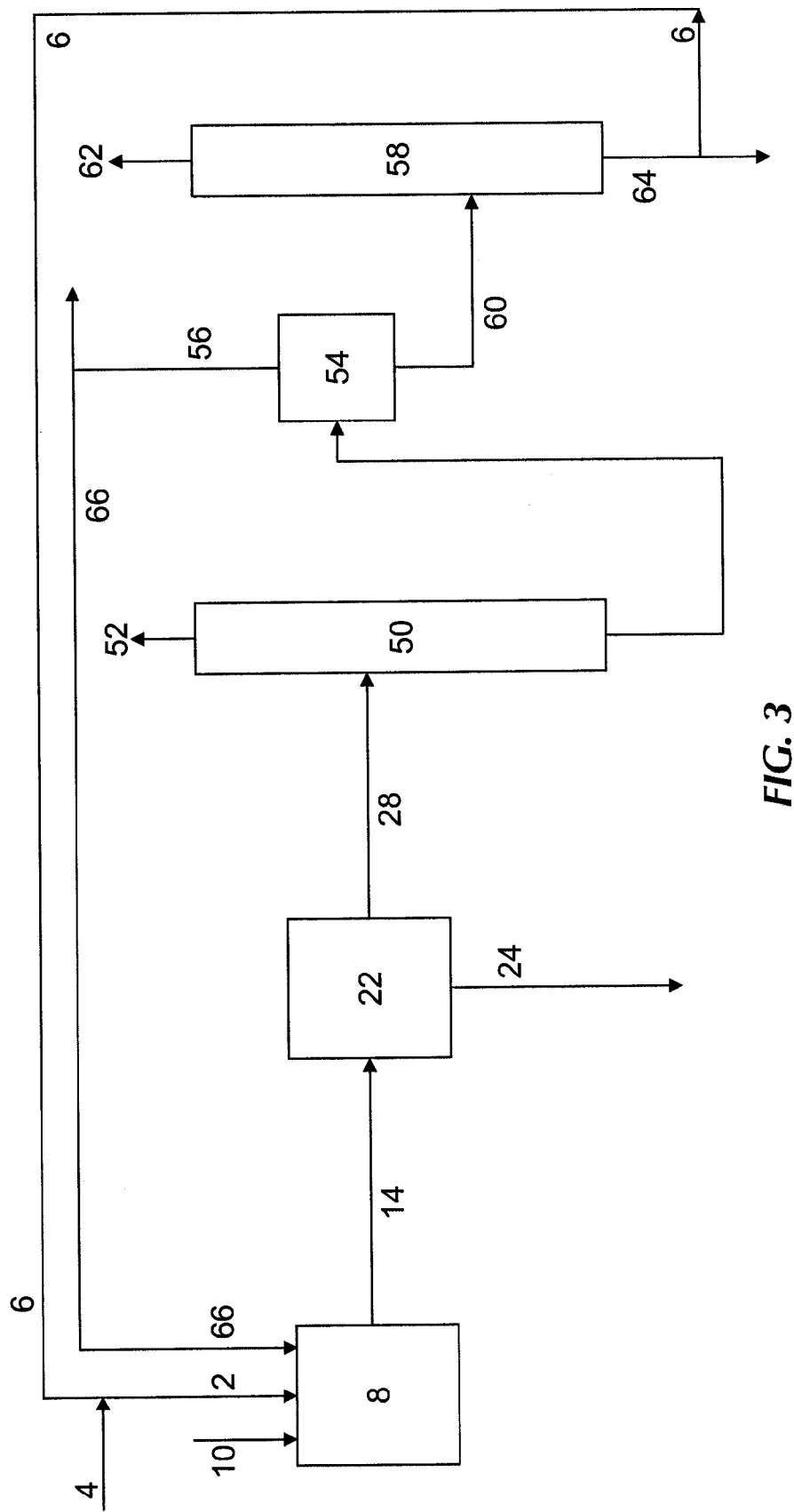
FIG. 3 is a simplified process flow diagram for oxidative dehydrogenation processes according to embodiments disclosed herein.

In the embodiment illustrated in FIG. 3, in lieu of recycling a portion of the water from quench unit 22, at least a portion of the nitrogen recovered via separation unit 54 may be recycled via flow line 66 as dilution gas to oxidative dehydrogenation reactor 8.

Figure 4:
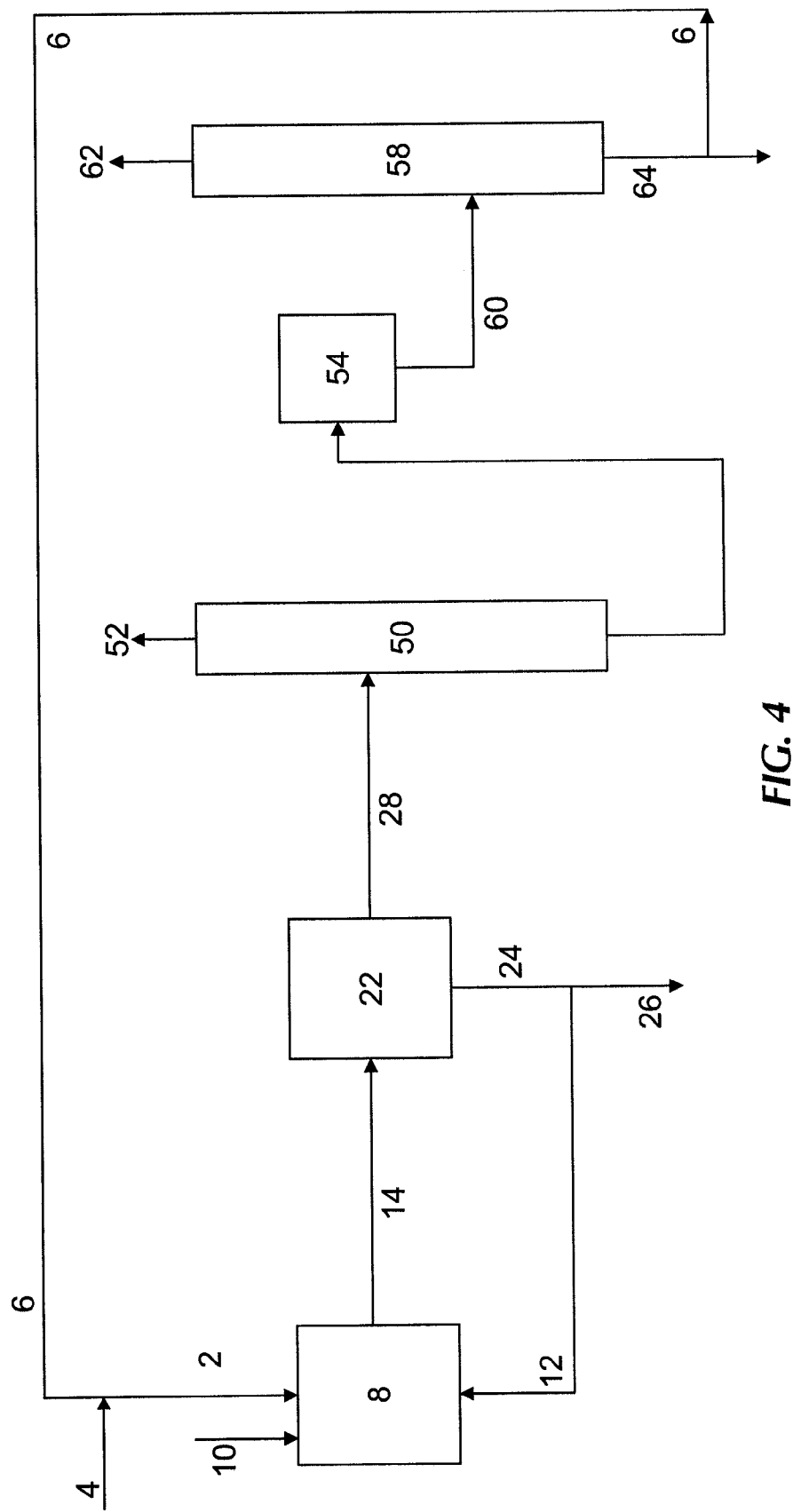
FIG. 4 is a simplified process flow diagram for oxidative dehydrogenation processes according to embodiments disclosed herein.

In the embodiment illustrated in FIG. 4, oxygen-containing gas stream 10 may include purified oxygen. As a result, it may be possible to simplify separation system 54 so as to not include nitrogen separation and recovery.

Although not illustrated in FIGS. 2-4, oxygen elimination reactors may be used as described above and with respect to FIG. 1. Other useful flow schemes are contemplated via embodiments disclosed herein.

EXAMPLES

Testing Procedures

Evaluation of catalysts for ethane oxydehydrogenation (ODH) is carried out in a fixed bed flow reactor. The feed compositions are various combinations of $C_2H_6/O_2/H_2O/N_2$, including molar ratios of: 10/10/10/70 (Feed A) and 15/10/10/65 (Feed B). A superficial space velocity of 1200 $h^{-1}$ is used, calculated based on volumetric flow rate of the reaction mixture at standard conditions of 1 atmosphere and 25° C., together with the reactor volume occupied by the catalyst. The reactor consists of 1.0 cm (0.4 inch) ID, stainless steel tube heated in an upright Lindberg furnace and at temperatures between 250 and 500° C. In this test the reactor contains 2.5 cc of the test catalyst of 12-20 mesh size. The reactor bed depth is approximately 3.0 cm (1.2 inches). In the test with extrudates, the particle size is 1.6 mm diameter×2.0 mm length, and, again, 2.5 cc of the particles are charged. All products are analyzed through an online GC system (Perkin Elmer CLARUS 500). The GC is equipped with two detectors, TCD and FID for two separate channels. One channel with the TCD is used to analyze $H_2$, $O_2$, CO, $CO_2$, and light hydrocarbons and the other channel with FID detector is used to analyze oxygenates and long-chain or aromatic hydrocarbons. Catalyst preparation Catalyst Preparation Comparative Example 1

A catalyst with a nominal composition $Mo_{1.0}.V_{0.43}Nb_{0.11}Sb_{0.07}Ca_{0.03}O_x$ is prepared in accordance to composition and preparation as disclosed in Example 1 of U.S. Pat. No. 4,524,236. 9.97 g of ammonium metavanadate is added to 100 mL of water and heated to 70° C. with stirring for fifteen minutes to form a solution (solution 1). Ammonium niobate (V) oxalate hydrate (20 wt % Nb contents) amounting to 10.56 g, antimony (III) oxalate amounting to 3.29 g and calcium nitrate tetrahydrate amounting to 1.77 g are added to a second 100 mL of water and heated to 70° C. with stirring for fifteen minutes and a slurry is obtained. This slurry is combined with solution 1 to form second slurry and the resulting slurry is heated at 70° C. with stirring for fifteen minutes. To a third 100 mL of water is added 35.3 g of ammonium heptamolybdate tetrahydrate and the mixture is heated to 70° C. with stirring to form a solution (solution 2) and this solution is added to the above slurry to form final mixture. The final mixture is also heated at 70° C. for fifteen minutes with stirring. The water is removed from the final mixture on a rotavapor at 50° C. to obtain a solid. The solid is further dried in an oven at 120° C. overnight and then oven calcined in air at a temperature of 350° C. for five hours. The X-ray diffractogram (XRD) of the calcined material mainly shows amorphous phase. The calcined material is ground with a mortar/pestle to powder which is then pressed and sized to 12-20 mesh granules for reactor evaluation. The catalyst is tested according to the above described test procedure and results are shown in Table 1.

Comparative Example 2

A catalyst with a nominal composition $Mo_{1.0}V_{0.43}Nb_{0.11}Sb_{0.07}Te_{0.03}O_x$ is prepared in accordance to Example 1 of U.S. Pat. No. 4,524,236 with Ca replaced by Te. The preparation procedure is the same as described for Comparative Example 1 except that 1.40 g of telluric acid is added in place of the calcium nitrate tetrahydrate Comparative Example 3

Low Temperature Calcinations

Figure 5:
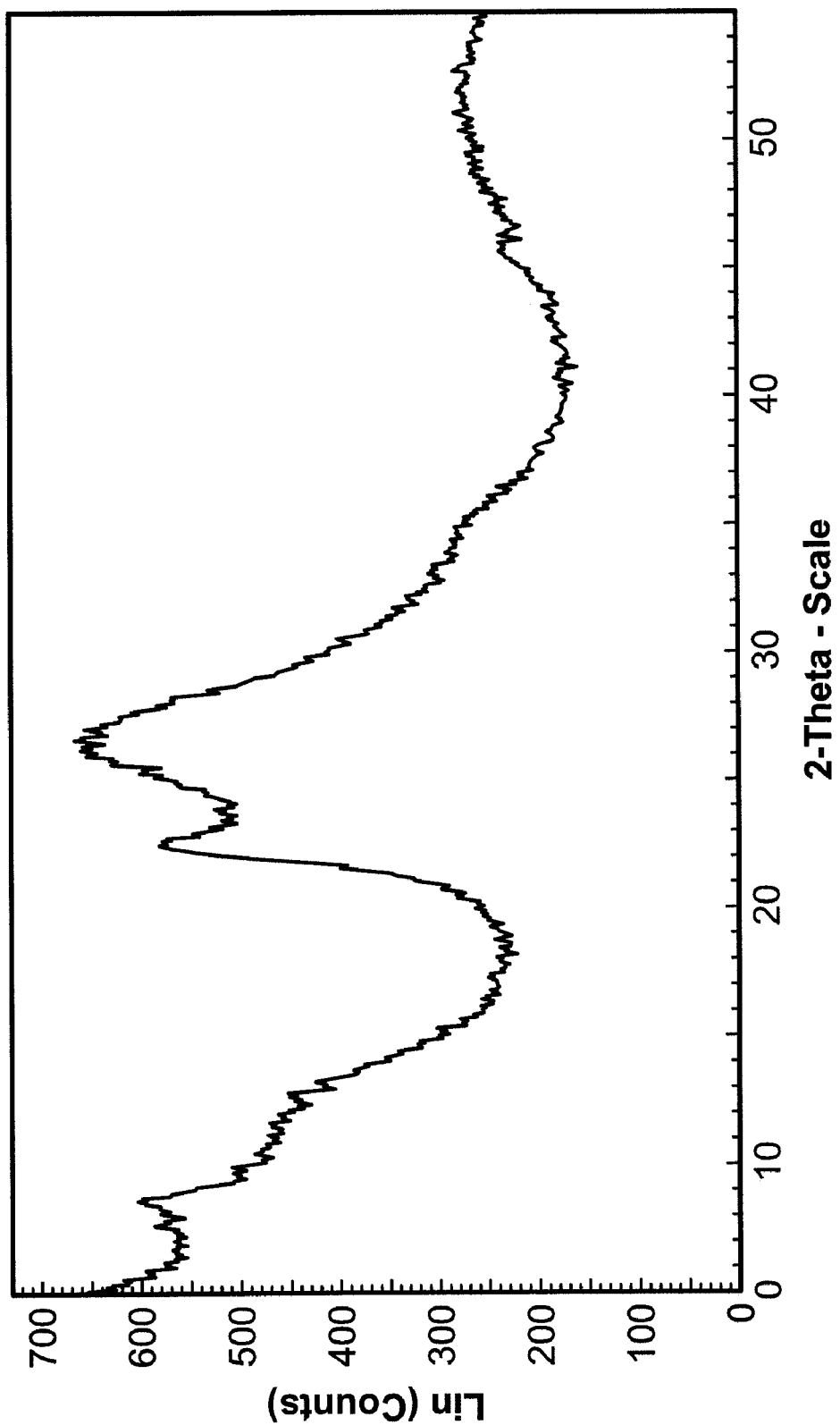
FIG. 5 is an X-ray diffractogram of a prior art catalyst.

A catalyst with a nominal composition $Mo_{1.0}V_{0.29}Nb_{0.17}Te_{0.21}Sb_{0.01}O_x$ is prepared using a different preparation procedure from Example 1 of U.S. Pat. No. 4,524,236 except for the calcination conditions. In a beaker 15.80 g of ammonium niobate (V) oxalate hydrate (20 wt % Nb contents), 0.5 g of antimony oxalate and 4.0 g of oxalic acid dihydrate are dissolved in 160 mL of DI water at room temperature and a homogeneous solution (solution 1) is obtained. In a round bottom flask, 35.60 g of ammonium heptamolybdate tetrahydrate, 6.72 g of ammonium metavanadate, 9.56 g of telluric acid are dissolved in 200 mL water at 70° C. to form a second solution (solution 2). 5.0 mL of concentrated nitric acid is added to Solution 2 and the resulting acidified solution is then combined with solution 1, obtaining an orange-colored gel. The water is removed from the gel on a rotavapor at 50° C. to obtain a solid. The solid is further dried in an oven at 120° C. overnight and a portion of the dried solid is calcined five hours in air at 350° C. The other portion of the dried solid is used in Example 1 for high temperature calcinations. The X-ray diffractogram (XRD) of the calcined solid mainly shows amorphous phase as illustrated in FIG. 5. The calcined material is ground with a mortar/pestle to powder which is then pressed and sized to 12-20 mesh granules for reactor evaluation.

Comparative Example 4

High Temperature Calcination in the Absence of $HNO_3$

A catalyst with a nominal composition $Mo_{1.0}V_{0.29}Nb_{0.17}Te_{0.21}Sb_{0.01}O_x$ is prepared in the absence of nitric acid in the following manner: In a beaker 7.90 g of ammonium niobate (V) oxalate hydrate (20 wt % Nb contents), 0.25 g of antimony oxalate and 2.0 g of oxalic acid dihydrate are dissolved in 80 mL of DI water at room temperature and a homogeneous solution (solution 1) is obtained. In a round bottom flask, 17.84 g of ammonium heptamolybdate tetrahydrate, 3.36 g of ammonium metavanadate, 4.78 g of telluric acid are dissolved in 100 ml water at 70° C., obtaining a second solution (solution 2). Solution 2 is combined with Solution 1 and an orange-colored gel is formed. The water is removed from the gel on a rotavapor at 50° C. to obtain a solid. The solid is further dried in an oven at 120° C. overnight and then calcined two hours in air at 275° C. followed by two hour calcinations at 600° C. in flowing nitrogen. The calcined material is ground with a mortar/pestle to powder which is then pressed and sized to 12-20 mesh granules for reactor evaluation.

Example 1

High Temperature Calcination in the Presence of $HNO_3$

Figure 6:
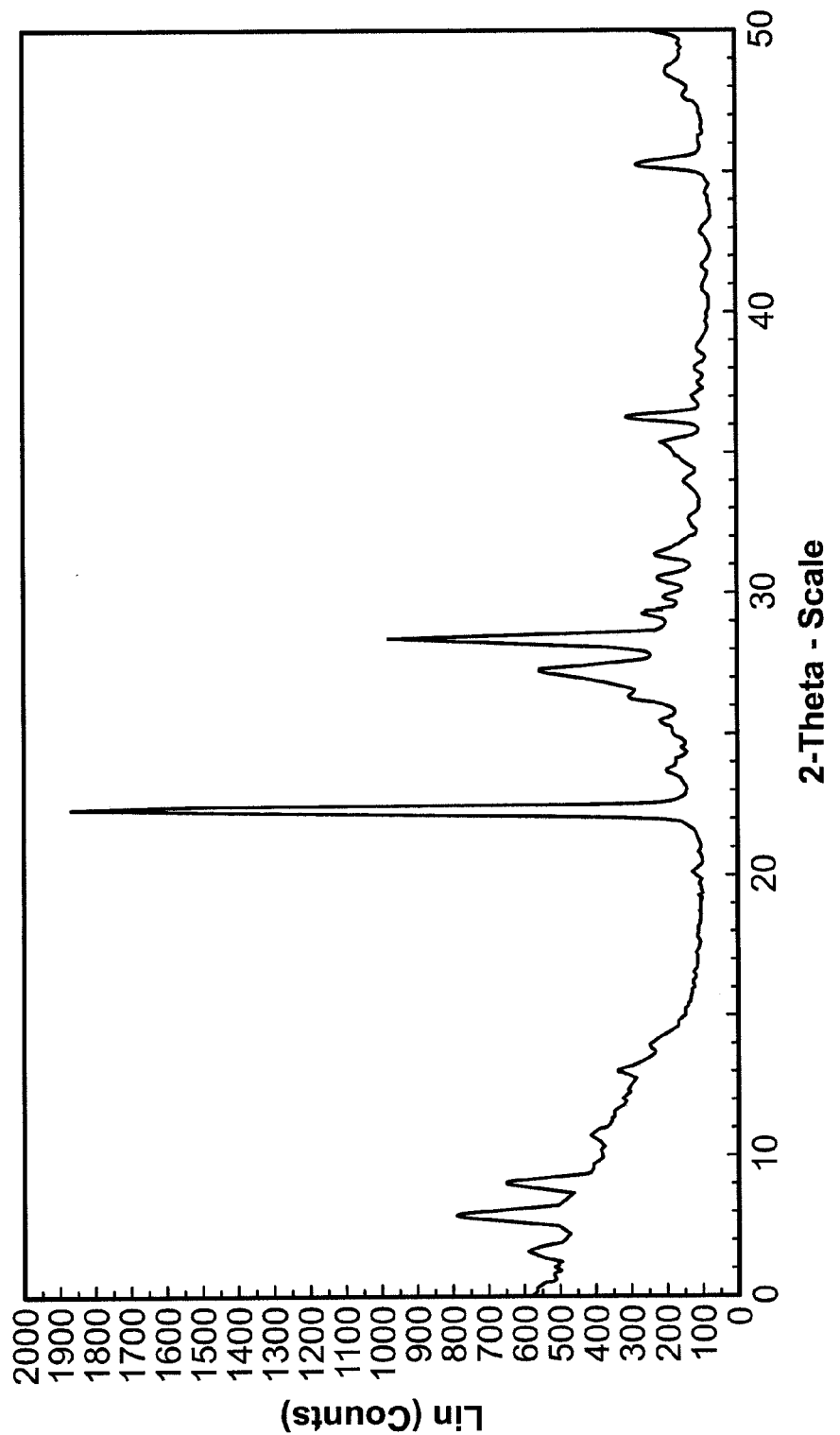
FIG. 6 is an X-ray diffractogram of a catalyst according to embodiments disclosed herein.

The portion of dried and uncalcined solid from Comparative Example 3 is first calcined two hours in air at 275° C. in an oven and then calcined two hours at 600° C. in flowing nitrogen. X-ray diffraction (XRD) of the calcined material shows the presence of two distinguished crystalline phases (hexagonal and orthorhombic phases) as illustrated in FIG. 6. The solid is ground with a mortar/pestle to powder and a portion of the powder is then pressed and sized to 12-20 mesh granules for reactor evaluation. The other portion of the powder is used for acid treatment as described in Example 3.

Example 2

The catalyst of Example 1 is tested with different feed composition as shown in Table 1.

Example 3

Figure 7:
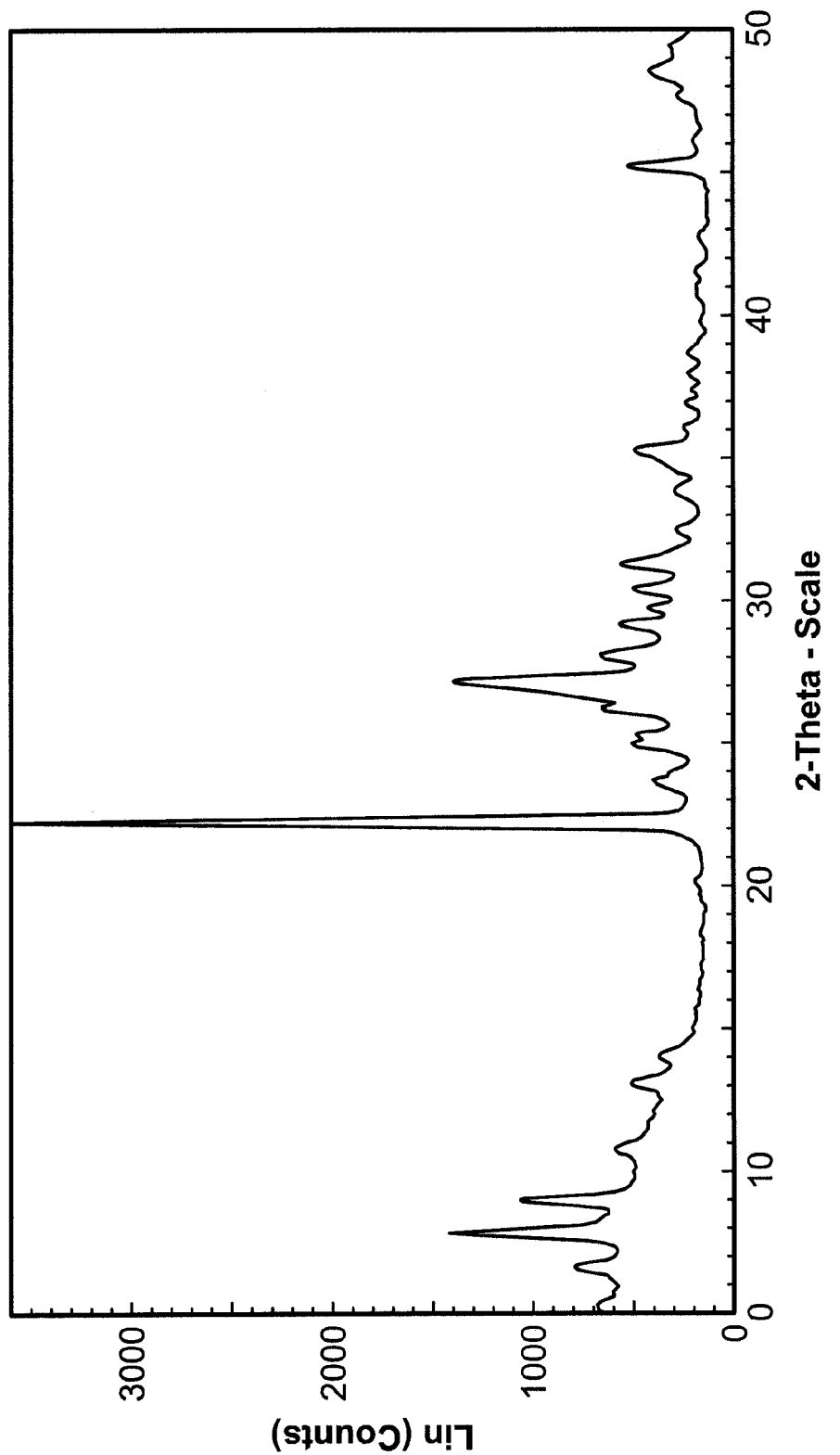
FIG. 7 is an X-ray diffractogram of a catalyst according to embodiments disclosed herein.

In a round bottom flask, 10 g of the powder of Example 1 are mixed with 10 g of oxalic acid dihydrate and 90 g of DI water. The resulting mixture is heated at 80° C. for five hours with stirring and then the solids is collected by vacuum filtration and dried in an oven at 120° C. overnight. The dried solid is heated two hours at 500° C. in flowing nitrogen. The X-ray diffractogram (XRD) of the acid-treated catalyst shows the presence of mainly one crystalline phase (orthorhombic phase) as illustrated in FIG. 7. The acid-treated catalyst is then pressed and sized to 12-20 mesh for reactor evaluation.

Example 4

High Sb

A catalyst with a nominal composition $Mo_{1.0}V_{0.29}Nb_{0.17}Te_{0.21}Sb_{0.07}O_x$ is prepared in the following: In a beaker, 7.90 g of ammonium niobate (V) oxalate hydrate (20 wt % Nb contents), 1.70 g of antimony oxalate and 2.0 g of oxalic acid dihydrate are mixed with 80 mL of DI water at room temperature and slurry is obtained. In a round bottom flask, 17.84 g of ammonium heptamolybdate tetrahydrate, 3.36 g of ammonium metavanadate, 4.87 g of telluric acid are dissolved in 100 mL water at 70° C. and a homogeneous solution is obtained. 2.5 mL of concentrated nitric acid is added to the solution and the resulting acidified solution is then combined with the slurry and an orange-colored gel is formed. The water is removed from the gel on a rotavapor at 50° C. and a solid is obtained. The solid is further dried in an oven at 120° C. overnight and then calcined two hours in air at 275° C. followed by two hour calcination at 600° C. in flowing nitrogen. The calcined material is ground with a mortar/pestle to powder which is then pressed and sized to 12-20 mesh granules for reactor evaluation.

Example 5

Low Te, 0.125 Level

A catalyst with a nominal composition $Mo_{1.0}V_{0.29}Nb_{0.17}Sb_{0.01}Te_{0.125}O_x$ is prepared in the following: In a beaker, 7.90 g of ammonium niobate (V) oxalate hydrate (20 wt % Nb contents), 0.25 g of antimony oxalate and 2.0 g of oxalic acid dihydrate are mixed with 80 mL of DI water at room temperature and homogeneous solution (solution 1) is obtained. In a round bottom flask, 17.83 g of ammonium heptamolybdate tetrahydrate, 3.43 g of ammonium metavanadate and 2.90 g of telluric acid are dissolved in 100 mL water at 70° C. and a homogeneous solution (solution 2) is obtained. 2.5 mL of concentrated nitric acid is added to Solution 2 and the resulting acidified solution is then combined with Solution 1 and an orange-colored gel is formed. The water is removed from the gel on a rotavapor at 50° C. and a solid is obtained. This solid is further dried in an oven at 120° C. overnight and then calcined two hours in air at 275° C. followed by two hour calcination at 600° C. in flowing nitrogen. The calcined material is ground with a mortar/pestle to powder which is then pressed and sized to 12-20 mesh granules for reactor evaluation.

Example 6

Low Te, 0.15 Level

A catalyst with a nominal composition $Mo_{1.0}V_{0.29}Nb_{0.17}Sb_{0.01}Te_{0.15}O_x$ is prepared following the same procedure as for Example 5 except that the amount of telluric acid is increased from 2.90 g to 3.41 g.

Example 7

Ni in Place of Sb

A catalyst with nominal composition $Mo_{1.0}V_{0.29}Nb_{0.17}Te_{0.10}Ni_{0.04}O_x$ is prepared in the following manner: In a beaker, 7.90 g of niobium oxalate and 2.0 g of oxalic acid dihydrate are dissolved in 80 mL DI water (solution 1) at room temperature and a homogeneous solution (solution 1) is formed. In a round bottom flask, 17.84 g of ammonium heptamolybdate tetrahydrate, 3.36 g of ammonium metavanadate, 2.32 g of telluric acid and 1.21 g of nickel nitrate hexahydrate are dissolved in 100 mL of DI water at 70° C. (solution 2). 2.5 mL of concentrated nitric acid is added to solution 2 and then combined with solution 1 to form a gel. The water is removed from the gel on a rotavapor at 50° C., obtaining a solid. The solid is further dried in an oven at 120° C. overnight and then calcined two hours in air at 275° C. followed by two hour calcination at 600° C. in flowing nitrogen. The calcined material is ground with a mortar/pestle to powder which is then pressed and sized to 12-20 mesh granules for reactor evaluation.

TABLE 1

| | | Test Condition | | Performance | | |
|---|---|---|---|---|---|---|
| Example | Catalyst | Feed | Temp (° C.) | $C_2$ % Conv | $C_2^-$ % Sel | $C_2^-$ % Yield |
| Comp. Ex. 1 | $Mo_{1.0}V_{0.43}Nb_{0.11}Sb_{0.07}Ca_{0.03}O_x$ | A | 400 | 67 | 62 | 42 |
| Comp. Ex. 2 | $Mo_{1.0}V_{0.43}Nb_{0.11}Sb_{0.07}Te_{0.03}O_x$ | A | 375 | 69 | 56 | 39 |
| Comp. Ex. 3 | $Mo_{1.0}V_{0.29}Nb_{0.17}Sb_{0.01}Te_{0.21}O_x$ | A | 375 | 44 | 76 | 33 |
| Comp. Ex. 4 | $Mo_{1.0}V_{0.29}Nb_{0.17}Sb_{0.01}Te_{0.21}O_x$ | A | 375 | 57 | 91 | 52 |
| Ex. 1 | $Mo_{1.0}V_{0.29}Nb_{0.17}Sb_{0.01}Te_{0.21}Ox$ | A | 380 | 74 | 89 | 66 |
| Ex. 2 | " | B | 390 | 70 | 91 | 64 |
| Ex. 3 | $Mo_{1.0}V_{0.29}Nb_{0.17}Sb_{0.01}Te_{0.21}Ox$ (Oxalic acid treated) | B | 380 | 71 | 92 | 65 |
| Ex. 4 | $Mo_{1.0}V_{0.29}Nb_{0.17}Sb_{0.07}Te_{0.21}O_x$ | A | 480 | 70 | 88 | 62 |
| Ex. 5 | $Mo_{1.0}V_{0.29}Nb_{0.17}Sb_{0.01}Te_{0.125}O_x$ | B | 360 | 67 | 93 | 62 |
| Ex. 6 | $Mo_{1.0}V_{0.29}Nb_{0.17}Sb_{0.01}Te_{0.15}O_x$ | B | 370 | 70 | 91 | 64 |
| Ex. 7 | $Mo_{1.0}V_{0.29}Nb_{0.17}Te_{0.10}Ni_{0.042}O_x$ | A | 390 | 71 | 87 | 62 |

Comparative Example 5

Unground Catalyst

The catalyst of Example 5 is reproduced in a larger scale and also several batches are prepared, combined and used for grinding, treatment with oxalic acid and extrusion as described in Examples 8-18. The preparation procedure is as follows: In a beaker, 15.82 g of ammonium niobate (V) oxalate hydrate (20 wt % Nb contents), 0.50 g of antimony oxalate and 4.0 g of oxalic acid dihydrate are mixed with 160 mL of DI water at room temperature and homogeneous solution (solution 1) is obtained. In a round bottom flask, 35.60 g of ammonium heptamolybdate tetrahydrate, 6.85 g of ammonium metavanadate and 5.80 g of telluric acid are dissolved in 200 mL water at 70° C. and a homogeneous solution (solution 2) is obtained. 5.0 mL of concentrated nitric acid is added to solution 2 and the resulting acidified solution is then combined with solution 1 and an orange-colored gel is formed. The water is removed from the gel on a rotavapor at 50° C. and a solid is obtained. This solid is further dried in an oven at 120° C. overnight and then calcined two hours in air at 275° C. followed by two hour calcination at 600° C. in flowing nitrogen. A portion of the calcined solid is pressed and sized to 12-20 mesh for reactor evaluation. The test results and BET surface area are shown in Table 2.

Example 8

Analytical Grinder 10 g of the calcined solid of Comparative Example 5 are ground with a Tekmar A-10 Analytical Mill: two minutes for every five grams. BET analysis of the ground powder shows 8.2 m²/g surface area. The powder is pressed and sized to 12-20 mesh for reactor evaluation.

Example 9

Cryogenic Grinding, 2 Min 50 g of the calcined solid of Comparative Example 5 are ground with a Freezer Mill (model #6770, Spex): two minutes for every five grams. BET analysis of the ground powder shows 9.0 m²/g surface area. A portion of the ground powder is pressed and sized to 12-20 mesh for reactor evaluation. The rest of the powder is used for treatment with oxalic acid as described in Examples 14-18.

Example 10

Cryogenic Grinding, 5 Min 10 g of the calcined solid of Comparative Example 5 are ground with a freezer/mill: five minutes for every five grams. BET analysis of the ground powder shows 16.2 m²/g surface area. The ground powder is pressed and sized to 12-20 mesh for reactor evaluation.

Example 11

Cryogenic Grinding, 10 Min 110 g of the calcined solid of Comparative Example 5 are ground with a freezer/mill: ten minutes for every five grams. BET analysis of the ground powder shows 17.3 m²/g surface area. A portion of the ground powder is pressed and sized to 12-20 mesh for reactor evaluation. The rest of the powder is used for extrusion as described in Example 12.

Example 12

Extrudate 100 g of the powder catalyst from Example 11 are mixed with 28 g of Ludox AS-40. The mixture is well mixed to form a doll which is then extruded with a Loomis Ram Extruder (model #232-16) and 1.6 mm extrudates are obtained. The extrudates are dried in an oven at 120° C. overnight and then calcined in flowing $N_2$ at 500° C. for two hours. The calcined materials are cut into ~2 mm in length for reactor evaluation.

Example 13

Catalyst is the same as for Example 12, but is tested at different temperature.

Table 2 summarizes the test results and BET surface areas for Examples 8-11 and test results only for Examples 12-13. All the tests are carried out under the conditions described previously and with a feed of $C_2H_6/O_2/H_2O/N_2=15/10/10/65$ molar.

TABLE 2

| Example | BET Surface Area (m²/g) | Temp (° C.) | Performance | | |
|---|---|---|---|---|---|
| | | | $C_2$ % Conv | $C_2^-$ % Sel | $C_2^-$ % Yield |
| Comp. Ex. 5 | 5.5 | 420 | 75 | 86 | 65 |

TABLE 2-continued

| Example | BET Surface Area (m²/g) | Temp (° C.) | Performance | | |
|---|---|---|---|---|---|
| | | | $C_2$ % Conv | $C_2^-$ % Sel | $C_2^-$ % Yield |
| Ex. 8 | 8.2 | 370 | 76 | 91 | 69 |
| Ex. 9 | 9.0 | 355 | 70 | 92 | 64 |
| Ex. 10 | 16.2 | 350 | 71 | 90 | 64 |
| Ex. 11 | 17.3 | 340 | 67 | 90 | 60 |
| Ex. 12 | | 380 | 69 | 87 | 60 |
| Ex. 13 | | 370 | 64 | 90 | 58 |

Example 14

Oxalic Acid Treatment, 1 g Acid/10 g Catalyst

In a round bottom flask, 10 g of the powder catalyst of Example 9 are mixed with 1 g of oxalic acid dihydrate and 99 g of DI water. The resulting mixture is heated at 80° C. for five hours with stirring. The solid is collected by vacuum filtration and dried in an oven at 120° C. overnight. The dried solid is pressed and sized to 12-20 mesh for reactor evaluation.

Example 15

Oxalic Acid Treatment, 5 g Acid/10 g Catalyst

In a round bottom flask, 10 g of the powder catalyst of Example 9 are mixed with 5 g of oxalic acid dihydrate and 95 g of DI water. The resulting mixture is heated at 80° C. for five hours with stirring. The solid is collected by vacuum filtration and dried in an oven at 120° C. overnight. The dried solid is pressed and sized to 12-20 mesh for reactor evaluation.

Examples 16-19

Oxalic Acid Treatment Followed by Annealing at 400° C.

The other portion of the dried solid of Example 15 is first pressed and sized to 12-20 mesh granules and then heated two hours at 400° C. in flowing nitrogen. The heat treated granules are evaluated at different temperatures.

Example 20

Oxalic Acid Treatment, 10 g Acid/10 g Catalyst

In a round bottom flask, 20 g of the powder catalyst of Example 9 are mixed with 20 g of oxalic acid dihydrate and 180 g of DI water. The resulting mixture is heated at 80° C. for five hours with stirring. The solid is collected by vacuum filtration and dried in an oven at 120° C. overnight. A portion of the dried solid is pressed and sized to 12-20 mesh for reactor evaluation.

Examples 21-22

Oxalic Acid Treatment Followed by Annealing at 500° C.

The other portion of the dried solid of Example 20 is first pressed and sized to 12-20 mesh granules and then heated two hours at 500° C. in flowing nitrogen.

Table 3 summarizes the test results for Examples 14-22. All the tests are carried out with a feed of $C_2H_6/O_2/H_2O/N_2=15/10/10/65$ molar.

TABLE 3

| Example | BET Surface Area (m²/g) | Performance | | |
|---|---|---|---|---|
| | | Temp (° C.) | $C_2$ % Conv | $C_2^=$ % Sel | $C_2^=$ % Yield |
| Ex. 14 | 12.3 | 340 | 72 | 92 | 66 |
| Ex. 15 | 22.4 | 320 | 70 | 93 | 65 |
| Ex. 16 | 16.3 | 298 | 35 | 97 | 34 |
| Ex. 17 | 16.3 | 310 | 45 | 96 | 43 |
| Ex. 18 | 16.3 | 320 | 55 | 95 | 52 |
| Ex. 19 | 16.3 | 330 | 65 | 93 | 60 |
| Ex. 20 | 21.4 | 320 | 69 | 91 | 63 |
| Ex. 21 | 10.2 | 350 | 72 | 92 | 66 |
| Ex. 22 | 10.2 | 360 | 81 | 89 | 72 |

As described above, catalysts useful for the oxidative dehydrogenation of hydrocarbons, such as ethylene, may be prepared according to embodiments disclosed herein. Such catalysts may allow a high selectivity to the desired olefin even at high hydrocarbon conversions. For oxidative dehydrogenation of ethane to ethylene, for example, catalysts prepared according to embodiments disclosed herein may result in selectivities of 85 mol %, 90 mol % or higher at ethane conversions of 60%, 65%, 70%, or higher.

Advantageously, ODH processes using catalysts prepared according to embodiments disclosed herein are thermodynamically favored, and may be carried out at much lower reaction temperatures (<450° C.) than steam cracking (which is generally in the range of 700-1000° C.), without the need for heat input to the reactor, and with no coke formation. The ODH production processes using the catalysts prepared according to embodiments disclosed herein obtain superior economics. Due to the high product selectivity and the other aspects of the resulting ODH process, catalysts disclosed herein significantly lower the net consumption of ethane feed and energy, plus significantly lower the investment cost for product separation/recovery. The combination of the process conditions and the catalysts disclosed herein may also result in acceptably low catalyst inventory/cost ratios and also excellent catalyst stability and life.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for forming a catalyst useful for the production of an olefin from a hydrocarbon, comprising:
   admixing at least one member selected from the group consisting of elemental metals and compounds to form a multi-metal composition comprising Mo, V, at least one member selected from the group consisting of Nb and Ta, at least one member selected from the group consisting of Te, Ga, Pd, W, Bi, and Al, and at least one of Ni and Sb;
   adjusting the pH of the multi-metal composition by adding nitric acid;
   drying the acidified multi-metal composition;
   calcining the dried multi-metal composition; and
   grinding the calcined multi-metal composition; and
   treating the ground multi-metal composition with acid.

2. The process of claim 1, further comprising at least one of sizing and shaping the ground multi-metal composition to form a mixed metal oxide catalyst.

3. The process of claim 1, further comprising annealing the acid-treated multi-metal composition.

4. The process of claim 1, wherein the catalyst has a general formula:

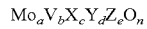

$$Mo_aV_bX_cY_dZ_eO_n$$

wherein:
   X=at least one member selected from the group consisting of Nb and Ta;
   Y=at least one member selected from the group consisting of Sb and Ni;
   Z=at least one member selected from the group consisting of the Te, Ga, Pd, W, Bi and Al;
   a=1.0;
   b=0.05 to 1.0;
   c=0.001 to 1.0;
   d=0.001 to 1.0;
   e=0.001 to 0.5; and
   n is determined by the oxidation states of the other elements.

5. The process of claim 1, further comprising admixing the at least one member selected from the group consisting of elemental metals and compounds of at least one of Fe, Co, Cu, Cr, Ti, Ce, Zr, Mn, Pb, Mg, Sn, Pt, Si, La, Ag and In to form the multi-metal composition.

6. The process of claim 5, wherein the catalyst has a general formula:

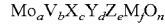

$$Mo_aV_bX_cY_dZ_eM_fO_n$$

wherein:
   X=at least one member selected from the group consisting of Nb and Ta;
   Y=at least one member selected from the group consisting of Sb and Ni;
   Z=at least one member selected from the group consisting of the Te, Ga, Pd, W, Bi and Al;
   M=at least one member selected from the group consisting of the Fe, Co, Cu, Cr, Ti, Ce, Zr, Mn, Pb, Mg, Sn, Pt, Si, La, K, Ag and In;
   a=1.0;
   b=0.05 to 1.0;
   c=0.001 to 1.0;
   d=0.001 to 1.0;
   e=0.001 to 0.5;
   f=0.001 to 0.3; and
   n is determined by the oxidation states of the other elements.

7. The process of claim 1, wherein the catalyst has a selectivity to olefin of at least 80 mole % at a paraffin conversion of at least 60% when used in an oxydehydrogenation process for conversion of a paraffin to an olefin.

8. The process of claim 7, wherein the olefin is ethylene and the paraffin is ethane.

9. The process of claim 8, wherein a selectivity to ethylene is at least 85 mole % at an ethane conversion of at least 65%.

10. The process of claim 8, wherein a selectivity to ethylene is at least 90 mole % at an ethane conversion of at least 70%.

11. The process of claim 1, further comprising:
   contacting at least one of the calcined composition and the sized composition with at least one member selected from the group consisting of the elemental metals and compounds including one member selected from the group consisting or more of Fe, Co, Cu, Cr, Ti, Ce, Zr, Mn, Pb, Mg, Sn, Pt, Si, La, K, Ag and In to form a second multi-metal composition; and calcining the second multi-metal composition to form a mixed metal oxide catalyst.

12. The process of claim 1, wherein the mixed metal oxide catalyst is supported on a solid.

13. The process of claim 12, wherein the solid comprises at least one member selected from the group consisting of silica, alumina, silica-aluminas, aluminosilicates, zirconia, titania, boria, zirconia toughened alumina, lithium aluminum silicates, silicon carbide, oxide-bonded silicon carbide, and mixtures thereof.

14. The process of claim 1, wherein the steps of grinding the multi-metal composition and treating with acid are performed substantially concurrently in a wet milling process.

15. A catalyst for oxydehydrogenating a paraffin to form an olefin formed by the process of claim 1.

16. A catalyst for oxydehydrogenating a paraffin to form an olefin, comprising:

$Mo_a V_b X_c Y_d Z_e O_x$, wherein:

X=at least one member selected from the group consisting of Nb and Ta;

Y=at least one member selected from the group consisting of Sb and Ni;

Z=at least one member selected from the group consisting of the Te, Ga, Pd, W, Bi and Al;

a=1.0;

b=0.05 to 1.0;

c=0.001 to 1.0;

d=0.001 to 1.0;

e=0.001 to 0.5;

n is determined by the oxidation states of the other elements; and wherein a selectivity to olefin is at least 85 mole % at a paraffin conversion of at least 60% and said catalyst is formed by the process of claim 1.

17. The catalyst of claim 12, further comprising $M_f$, wherein

M is at least one member selected from the group consisting of Ni, Fe, Co, Cu, Cr, Ti, Ce, Zr, Mn, Pb, Mg, Sn, Pt, Si, La, K, Ag and In; and f=0.001 to 0.3.

18. The catalyst of claim 16, wherein the olefin is ethylene and the paraffin is ethane.

19. The catalyst of claim 18, wherein a selectivity to ethylene is at least 85 mole % at an ethane conversion of at least 65%.

20. The catalyst of claim 18, wherein a selectivity to ethylene is at least 90 mole % at an ethane conversion of at least 70%.

* * * * *